(12) United States Patent
Van Jaarsveld

(10) Patent No.: US 9,974,309 B2
(45) Date of Patent: May 22, 2018

(54) FLOWER PRESERVATION METHOD AND DEVICE

(71) Applicant: Tessara (Pty) Ltd, Cape Town (ZA)

(72) Inventor: Alwyn Jacobus Van Jaarsveld, Bellville (ZA)

(73) Assignee: Tessara (Pty) Ltd, Cape Town (ZA)

( * ) Notice: Subject to any disclaimer, the term of this patent is extended or adjusted under 35 U.S.C. 154(b) by 0 days. days.

(21) Appl. No.: 15/308,913

(22) PCT Filed: May 6, 2015

(86) PCT No.: PCT/IB2015/053303
§ 371 (c)(1),
(2) Date: Nov. 4, 2016

(87) PCT Pub. No.: WO2015/170264
PCT Pub. Date: Nov. 12, 2015

(65) Prior Publication Data
US 2017/0071209 A1 Mar. 16, 2017

(30) Foreign Application Priority Data
May 6, 2014 (ZA) .................. 2014/03242

(51) Int. Cl.
*A01N 3/02* (2006.01)
*A01N 59/02* (2006.01)
*B65B 11/00* (2006.01)
*B65B 25/02* (2006.01)
*B65D 81/24* (2006.01)
*B65D 85/50* (2006.01)

(52) U.S. Cl.
CPC .............. *A01N 59/02* (2013.01); *A01N 3/02* (2013.01); *B65B 11/004* (2013.01); *B65B 25/023* (2013.01); *B65D 81/24* (2013.01); *B65D 85/50* (2013.01); *B65D 85/505* (2013.01)

(58) Field of Classification Search
CPC ........ A01N 3/02; A01N 59/02; B65B 11/004; B65B 25/023; B65D 81/24; B65D 85/50; B65D 85/505
See application file for complete search history.

(56) References Cited

U.S. PATENT DOCUMENTS

| | | | |
|---|---|---|---|
| 3,502,485 A | 3/1970 | Illouze | |
| 2005/0106380 A1 | 5/2005 | Gray et al. | |

FOREIGN PATENT DOCUMENTS

| | | |
|---|---|---|
| GB | 1002867 | 9/1965 |
| GB | 2189676 | 11/1987 |
| WO | 94/10233 | 5/1994 |
| WO | 2006/129172 | 12/2006 |
| WO | 2011/143564 | 11/2011 |

OTHER PUBLICATIONS

International Preliminary Report on Patentability in related PCT Application Serial No. PCT/IB2015/053303, dated Nov. 8, 2016.
International Search Report in related PCT Application Serial No. PCT/IB2015/053303, dated Jul. 20, 2015.

*Primary Examiner* — John Pak
*Assistant Examiner* — Nathan W Schlientz
(74) *Attorney, Agent, or Firm* — Hovey Williams LLP

(57) ABSTRACT

This invention relates to a method of preserving one or more cut flowers with the use of a sulphur dioxide ($SO_2$) generating device. The method further relates to an $SO_2$ generating device for the preservation of one or more cut flowers. The device may be in the form of a strip for attachment to a flower sleeve or in the form of an article of any shape for placement inter-bunch and above the flower heads.

10 Claims, 3 Drawing Sheets

FLOWER PRESERVATION METHOD AND DEVICE

RELATED APPLICATIONS

This application is the National Stage of International Patent Application No. PCT/IB2015/053303, filed 6 May 2015, which is hereby incorporated by reference in its entirety, and which claims priority to South African Patent Application No. 2014/03242 filed 6 May 2014.

BACKGROUND OF THE INVENTION

This invention relates to a method of preserving one or more cut flowers with the use of a sulphur dioxide ($SO_2$) generating device. The method further relates to an $SO_2$ generating device for the preservation of one or more cut flowers. The device may be in the form of a strip for attachment to a flower sleeve or in the form of an article of any shape for placement inter-bunch and above the flower heads.

The cut flower industry is a fast-growing, global industry, which in recent years has shown a global trade volume of over US$100 billion.

The loss of flowers susceptible to fungal infection, including *Botrytis* has resulted in millions of lost revenue by flower sellers.

Present methods for preservation of flowers include dipping of the flower heads in antimicrobial solution such as commercial bleach, followed by drying, or treatment of the water holding the flower stems with a solution comprising various components including bleach, sugar, various antifungal chemicals and the like.

However, there is currently no product that actively prevents *Botrytis* growth on flower heads during the retail phase or during so-called "wet" transport in buckets.

The "dipping" technique is only applied prior to transport and has a limited period of efficacy, and sulphur dioxide based products and potassium permanganate based products have only been applied successfully in enclosed cartons during dry transport, also limiting the period of efficacy.

A device for effective preservation of the flower heads of cut flowers for use during wet transport and during the retail phase while the flowers are displayed in buckets that extends their shelf life would therefore be greatly beneficial.

SUMMARY OF THE INVENTION

According to a first embodiment of the invention, there is provided a method of preserving one or more cut flowers with the use of a sulphur dioxide ($SO_2$) generating device. The device may be in the form of a strip for attachment to an end of a flower sleeve or in the form of an article of any shape for placement within the bunch and above the flower heads.

The method may comprise the steps of:
(i) providing one or more cut flowers;
(ii) providing a flower sleeve having a $SO_2$ generating strip affixed at one end for wrapping the one or more cut flowers and wrapping the flower sleeve around the cut flowers, such that the end to which the $SO_2$ generating strip is affixed is adjacent to, but not in direct contact with, one or more flower heads of the cut flowers contained within the flower sleeve; and/or
(iii) positioning an $SO_2$ generating article of any shape within the cut flowers and above the one or more flower heads, such that the article is above, but not in direct contact with, the flower heads of the cut flowers.

Typically, the article may be positioned above the flowers by affixing the article to an end of an elongate member, whereby the length of the elongate member is positioned within the cut flowers and the affixed article is held above the cut flower heads on the end of the elongate member. The article may be affixed to the elongate member by either an adhesive means or a mechanical means. For example, the article may be affixed to the elongate member by means of glue, a clasp mechanism or staples. For example, the elongate member may be a floral cardholder or similar device.

Typically, the $SO_2$ generating strip is affixed to an inner face of the flower sleeve end adjacent to, but not in direct contact with the one or more flower heads. The $SO_2$ generating strip may be affixed to the sleeve by either an adhesive means or a mechanical means. For example, the $SO_2$ generating strip may be affixed to the sleeve by means of glue or staples.

The method of preservation may comprise inhibition of growth of a microbial organism. For example, the microbial organism may be a fungal organism such as *Botrytis*.

According to a further embodiment of the invention, there is provided a $SO_2$ generating strip for attachment to a flower sleeve or an $SO_2$ generating article for affixing to an elongate member, such as a floral cardholder, for positioning together or within one or more cut flowers, the strip or article comprising a substance which in the presence of moisture generates $SO_2$. Such a substance is well known to those in the art and may be sodium metabisulphate, an acidic mixture comprising sodium metabisulphate and fumaric acid, an acidic mixture comprising sodium sulphite and potassium bitartrate, or a mixture of both of the acidic mixtures.

The $SO_2$ generating strip may have a width such that when affixed to a flower sleeve containing one or more cut flowers it extends from the end of the flower sleeve to the top of one or more flower heads of the cut flowers contained in the flower sleeve such that the $SO_2$ generating strip is not in direct contact with the one or more flower heads. Typically, the width of the $SO_2$ generating strip is about 22 mm. However, it is to be appreciated that the width of the strip may vary depending on the length of the flower sleeve and the depth of placement of the one or more cut flowers in the flower sleeve when in use.

Typically, the total area of the $SO_2$ generating article is about 50 $mm^2$, but the total area may vary from less than this to about two or three times this area. It is to be appreciated that the shape and dimentions of the $SO_2$ generating article may vary depending on a number of factors, including but not limited to: the concentration of $SO_2$ comprised in the $SO_2$ generating article, the surface area of the cut flower heads required to be treated or the number of cut flowers, aesthetic considerations of the user, type or variety of flower(s) used within the bunch, amount of foliage present in the bunch in relation to the amount of flowers/petals, and temperature of the bunch during transport, storage and/or display. Such factors would be a matter of routine experimentation to determine.

According to a further embodiment of the invention, there is provided a composite $SO_2$ generating device for use in the preservation of one or more cut flowers, which may be in the form of:
a flower sleeve comprising a $SO_2$ generating strip at one end, or
(ii) a holder comprising an elongate member, such as a flowercard holder, having a $SO_2$ generating article of any shape affixed at one end, or integrally formed on one end of the elongate member.

Typically, the flower sleeve comprises a SO₂ generating strip affixed to an inner face of the flower sleeve end which in use is adjacent to, but not in direct contact with, one or more flower heads of one or more cut flowers contained within the sleeve. The SO₂ generating strip may be affixed to the sleeve by either an adhesive means or a mechanical means. For example, the SO₂ generating strip may be affixed to the sleeve by means of glue or staples. Alternatively, the SO₂ generating strip may be integrally formed with the flower sleeve.

Typically, the holder is positioned such that the length of the elongate member is within the cut flowers and the SO₂ generating article is held above the cut flower heads when in use. The article may be affixed to the elongate member by either an adhesive means or a mechanical means. For example, the article may be affixed to the elongate member by means of glue, a clasp mechanism or staples. Alternatively, the SO₂ generating article may be integrally formed on the end of the elongate member.

The cut flowers may be any cut flower that is susceptible to *Botrytis* infection. Preferably, the cut flowers may be selected from the group consisting of roses, chrysanthemums or gerberas.

DETAILED DESCRIPTION OF THE INVENTION

Figure 1A:
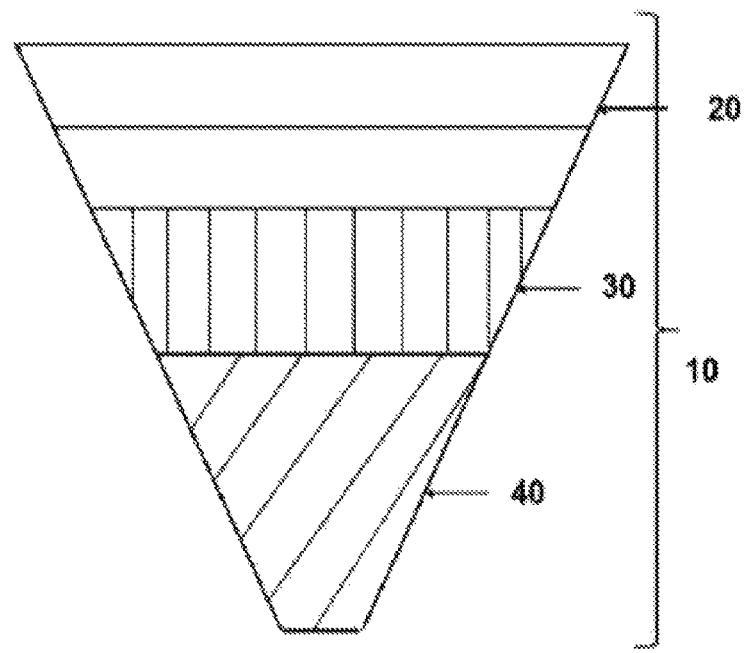
FIG. 1(A) shows a representative illustration of a side view of a flower sleeve containing a bunch of flowers with a SO₂ generating strip of the invention at the top end of the flower sleeve, and (B) shows a representative illustration of a bunch of flowers into which a holder comprising an SO₂ generating article of the invention has been positioned.
Figure 1B:
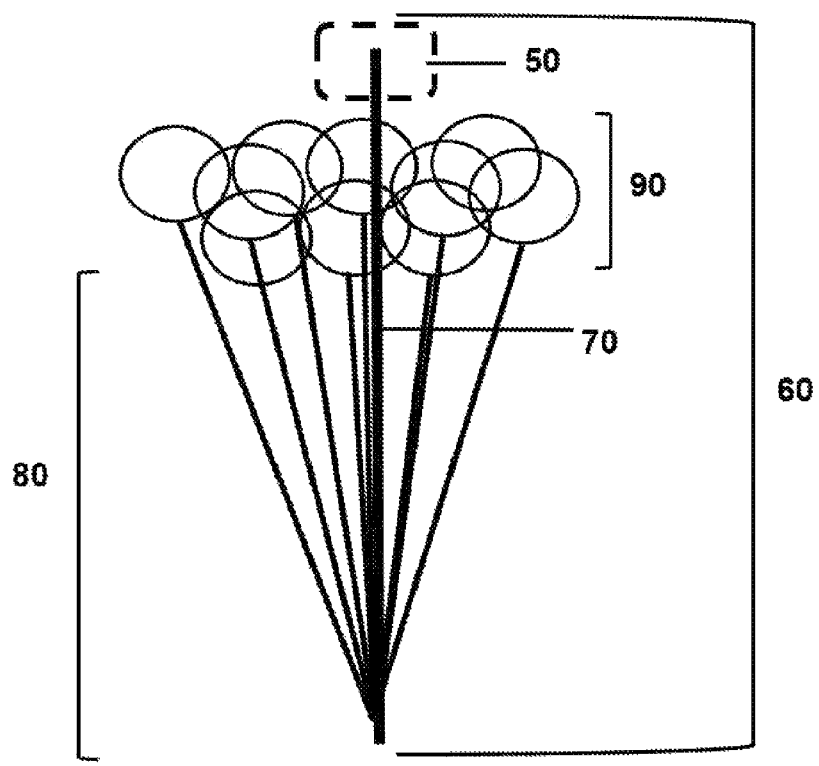

The current invention provides a method of preserving one or more cut flowers with the use of a sulphur dioxide (SO₂) generating device. The method further relates to an SO₂ generating device for the preservation of one or more cut flowers. The device may be in the form of a strip for attachment to a flower sleeve or in the form of an article of any shape for placement inter-bunch and above the flower heads.

There is presently no means of preserving the flower head of cut flowers during wet transport in buckets, or during the retail phase when the flowers are displayed in a store. As a result, fungal infection, in particular *Botrytis* infection, can set in during this period, resulting in damage to the flower head and the flower or even entire flower bunch must then be discarded resulting in a financial loss to the retailer.

The applicant sought to develop a method that could be used to preserve cut flowers from microbial growth, in particular fungal infection, such as *Botrytis* in a flower bunch, either within a flower sleeve or not, for use either during wet transport in a bucket or during display in a store. The applicant determined that surprisingly, it was possible to preserve the flower heads of the cut flowers with the use of a sulphur dioxide (SO₂) generating device, either in the form of an SO₂ generating strip affixed to the top end of a sleeve containing the cut flowers, or with the use of a SO₂ generating article positioned above the flower heads by means of an elongate member, or by the use of both the strip and the article.

The use of the strip comprises the steps of firstly producing or providing a flower sleeve, such as a paper or plastic flower sleeve used by commercial flower sellers for wrapping one or more cut flowers, in particular those susceptible to fungal infection, such as *Botrytis* infection, including roses, chrysanthemums, gerberas or the like, the flower sleeve (10) comprising a SO₂ generating strip at one end (20).

The SO₂ generating strip (20) is typically affixed to an inner face of the flower sleeve end adjacent to, but not in direct contact with the one or more flower heads (30). The SO₂ generating strip may be affixed to the sleeve by either an adhesive means or a mechanical means. For example, the SO₂ generating strip (20) may be affixed to the sleeve (10) by means of glue or staples, or other means known to those skilled in the art. Alternatively, the strip may be integrally formed with the flower sleeve.

Next, one or more cut flowers are wrapped in the flower sleeve, according to standard practice. When wrapping the cut flowers, the flower sleeve is positioned such that the SO₂ generating strip (20) is in close proximity or adjacent to the one or more flower heads (30) of one or more cut flowers contained within the flower sleeve but opposed to the flower stems and leaves (40). The SO₂ generating strip (20) must not be in direct contact with the flower heads (30).

In practice, the method of wrapping one or more cut flowers in a flower sleeve results in a generally conical flower sleeve with the narrow end of the cone enclosing the base of the flower stem(s) which extend from the bottom of the sleeve and are placed in water with or without a flower treatment solution. The opposed open top end of the flower sleeve encloses but is not in contact with the flower head(s). A representative illustration of one embodiment of the flower sleeve of the invention, with the SO₂ generating strip (20) and containing a bunch of roses is shown in FIG. 1A. Accordingly, when affixed to the open top end of the flower sleeve, the SO₂ generating strip is inherently not in direct contact with the flower head(s). There may optionally be a space provided between the top of the flower head(s) (30) and the end of the SO₂ generating strip (20) when viewed from the side.

The use of the SO₂ generating article (50) comprises the steps of producing or providing a holder (60) comprising the SO₂ generating article (50) affixed one end of an elongate member (70), such as a floral cardholder and placing the length of the elongate member (70) of the holder (60) adjacent or within one or more cut flower stems (80) such that the SO₂ generating article (50) is above and not in contact with the flower heads (90) of the one or more cut flowers. Typically, the SO₂ generating article is positioned substantially centrally in the cut flower bunch.

The SO₂ generating article or strip may be printed on, embellished or decorated and may be any colour desired by the user. The $SO_2$ generating article may further be any shape or dimention desired by the user.

It is possible to use both the sleeve comprising the $SO_2$ generating strip and the holder comprising the $SO_2$ generating article with the cut flowers at the same time if desired.

The $SO_2$ generating strip or article of the invention typically comprises a substance which in the presence of moisture generates $SO_2$. Such a substance is well known to those in the art and may be sodium metabisulphate, an acidic mixture comprising sodium metabisulphate and fumaric acid, an acidic mixture comprising sodium sulphite and potassium bitartrate, or a mixture of both of the acidic mixtures.

$SO_2$ generating strips or articles can be processed by cutting $SO_2$ generating sheets known to those skilled in the art to the desired shape and dimentions. Any cutting technique known to those skilled in the art that utilizes a sharp blade and does not produce frayed edges, product delamination, crystallization, melting, activation, discolouration or contamination as an effect during or after the process may be used. Although any $SO_2$ generating sheet which in the presence of moisture generates $SO_2$, may be used, but sheets produced as disclosed in the published patents ZA8900691, ZA9507170 and U.S. Pat. No. 7,045,182 are preferably used for generation of the $SO_2$ generating strips or articles of the invention.

The $SO_2$ generating strip may have a width such that when affixed to a flower sleeve containing one or more cut flowers it extends from the end of the flower sleeve to the top or near the top of one or more flower heads of the cut flowers contained in the flower sleeve. There may optionally be a space provided between the top of the flower head(s) (30) and the $SO_2$ generating strip (20). Of importance, is that the $SO_2$ generating strip (20) is not in direct contact with the one or more flower heads (30). Typically, the width of the $SO_2$ generating strip is about 22 mm. However, it is to be appreciated that the width of the strip may vary depending on the length of the flower sleeve and the depth of placement of the one or more cut flowers in the flower sleeve when in use.

Furthermore, the $SO_2$ generating strip may have any length. For example, it may be the length or near length of the open top end of a flower sleeve and provided as multiple strips to producers of flower sleeves or flower sellers using flower sleeves for affixing one strip each to the top of a sleeve. Alternatively, it may be provided as a role of a length suitable for cutting into a plurality of strips, each strip once cut, having the length or near the length of one end of a flower sleeve.

Typically, the total area of the $SO_2$ generating article is about 50 $mm^2$, but the total area may vary from less than this to about two or three times this area. It is to be appreciated that the shape and dimentions of the $SO_2$ generating article may vary depending on a number of factors, including but not limited to: the concentration of $SO_2$ comprised in the $SO_2$ generating article, the surface area of the cut flower heads required to be treated or the number of cut flowers, aesthetic considerations of the user, type or variety of flower(s) used within the bunch, amount of foliage present in the bunch in relation to the amount of flowers/petals, and temperature of the bunch during transport, storage and/or display. Such factors would be a matter of routine experimentation to determine.

Although the production of the flower sleeve of the invention may comprise a step of attaching the $SO_2$ generating strip to the flower sleeve by adhesive or mechanical means after making or obtaining the flower sleeve, the $SO_2$ generating strip may also be integrally formed with the flower sleeve during the manufacturing process of the sleeve. Similarly, the production of the holder may comprise a step of attaching the $SO_2$ generating article to an end of the elongate member by adhesive or mechanical means after making or obtaining the elongate member, for example by gluing, stapling or a clasp mechanism, the $SO_2$ generating article may also be integrally formed with the end of the elongate member of the holder.

The invention will be described by way of the following examples which are not to be construed as limiting in any way the scope of the invention.

EXAMPLES

Example 1

Manufacture of the $SO_2$ Generating Strip $SO_2$ generating strips were processed by cutting $SO_2$ generating sheets to the desired strip width and length by means of a sharp blade. Manufacture of the $SO_2$ generating sheets does not form part of this invention, and any $SO_2$ generating sheet which in the presence of moisture generates $SO_2$, may be processed to an $SO_2$ generating strip of the invention. In this example, sheets produced as disclosed in the published patents ZA8900691, ZA9507170 and U.S. Pat. No. 7,045,182 were processed into $SO_2$ generating strips of the invention.

Example 2

Manufacture of Plastic Flower Sleeves Comprising a $SO_2$ Generating Strip

Standard commercial plastic flower sleeves were used for manufacture of the $SO_2$ generating plastic sleeves. Plastic flower sleeves are typically wrapped around flower bunches to form a generally cone-shaped sleeve enclosing the flower bunch, with the base of the cone-shaped sleeve having the narrowest diameter being wrapped around the base of the cut flower stems, and the diameter of the sleeve then broadening with the top of the cone-shaped sleeve having the broadest diameter adjacent to or slightly above the flower heads.

In this experiment, a $SO_2$ generating strip of about 20 mm in width was affixed to or near the top of each plastic sleeve such that it was in close proximity to the flower heads, but not in direct contact with the flower heads.

Furthermore, the $SO_2$ generating strip was affixed to run the entire length or near the entire length of the top opening of the flower sleeve. However, the width of the strip and position of the strip in the sleeve may be selected dependent on the length of the flower sleeve and the depth of placement of the flowers in the sleeve, with the proviso that the $SO_2$ generating strip must be in close proximity to the flower heads but not the stems or leaves of the cut flowers. This is because the leaves and stems have a much higher count of stomata than flower heads and respire at a much higher rate due to the presence of photosynthesizing tissues and therefore are more at risk from $SO_2$ burn and/or bleach than flower petals.

The $SO_2$ generating strips were simply stapeled to the inner surface of the plastic sleeve for enclosing a flower bunch. However, the $SO_2$ generating strips may be affixed by any suitable means known to those skilled in the art, including by an adhesive means such as glue.

Example 3

Rose Flower Trial

1. Objective

The objective of the trial was to test the performance of a $SO_2$ generating strip affixed to a flower sleeve containing commercially grown and packaged cut flowers for use as an active control mechanism against *Botrytis cinerea* on rose (*Rosa* sp.).

2. Materials and Methods

Export quality roses from the northern region of South Africa (North West Province) were used in the trial. Eight different rose varieties were tested: Coolwater, Mantra, Tropical Amazon, Bibi, Red One, Bella Rose, Avalanche and Vandela. The flowers were grown under greenhouse conditions, harvested, handled and packed as for export and sent to the Cape Town depot of a large commercial rose supplier in South Africa.

The roses were packed dry in standard rose cartons. Each carton contained 8 varieties with 3 bunches of 10 stems per variety packed to bring the final total to 240 stems. The buds of each bunch were protected by a sleeve of corrugated carton to limit mechanical damage.

After arrival at the commercial flower supplier in Cape Town, the cartons were transported intact to a cold room at the testing facility where the cartons were stored for a further 24 hours at 4° C. This was done to simulate a total period of cooled in-box transport of 72 hours.

The roses were removed after this period of simulated export and placed in 10 L buckets containing 3 L of water for 72 hours to mimic the three days normally spent under supermarket conditions. Specifically, the corrugated sleeves surrounding each bunch of each variety of roses were removed and replaced with either a plastic flower sleeve alone, or a plastic flower sleeve to which the $SO_2$ generating strip was affixed at or near the top of the sleeve. Accordingly, each variety was tested either with or without a $SO_2$ generating sleeve.

Stems were shortened by cutting off 2 cm from the base of the stem as is normal practice before placing the sleeve-enclosed flower bunches in the buckets containing water. The water was treated with 1 ml per liter of a commercial rose solution (specifically, Chrysal RVB and a Chrysal T-bag for use in 3 liter of water). The buckets containing the flower sleeves with the $SO_2$ generating strips were stored at room temperature (20° C.) with a relative humidity of 70%.

Following the simulated in-store period, the cut flower bunches had their sleeves and rubber bands removed and each bunch of 10 stems were placed in a separate vase for 7 days to simulate the display of roses in the home environment. The water in the vases contained a standard commercially available cut flower solution for roses.

The different test and control rose varieties were evaluated on five separate occasions, firstly on the last day of simulated in-store storage (i.e. day 3 post transport phase), then on the first, third, fifth and seventh day of the simulated home-display period (i.e. days 4, 6, 8 and 10 post transport phase. The flower heads were evaluated for any signs of damage, including signs of Botrytis, bruising and $SO_2$ burn.

Flowers were not artificially inoculated with Botrytis, but the trial was conducted during a period of the year when weather conditions were suitable for the development of *Botrytis*. The 8 varieties of rose used were cultivars known to be more sensitive to *Botrytis*.

Flowers were inspected for signs of *Botrytis* and these included spots of infection, petals with brown or tan blotches indicating a spreading infection as well as well-established infections where the entire flower head wilts, turns brown and in some cases detaches from the flower stem.

Flower damage was scored from 1 to 3 according to typical practice, where a score of 1 indicates that damage is present, but a non-trained eye will not detect it, a score of 2 indicates that the damage is visible to most people, but does not detract from the overall appearance of the bunch and a score of 3 indicates that the damage is of such severity that the flower step needs to be removed from the bunch.

Accordingly, each bunch of 10 stems is given a total score based on the level of damage present in each stem.

3. Results and Discussion

Figure 2:
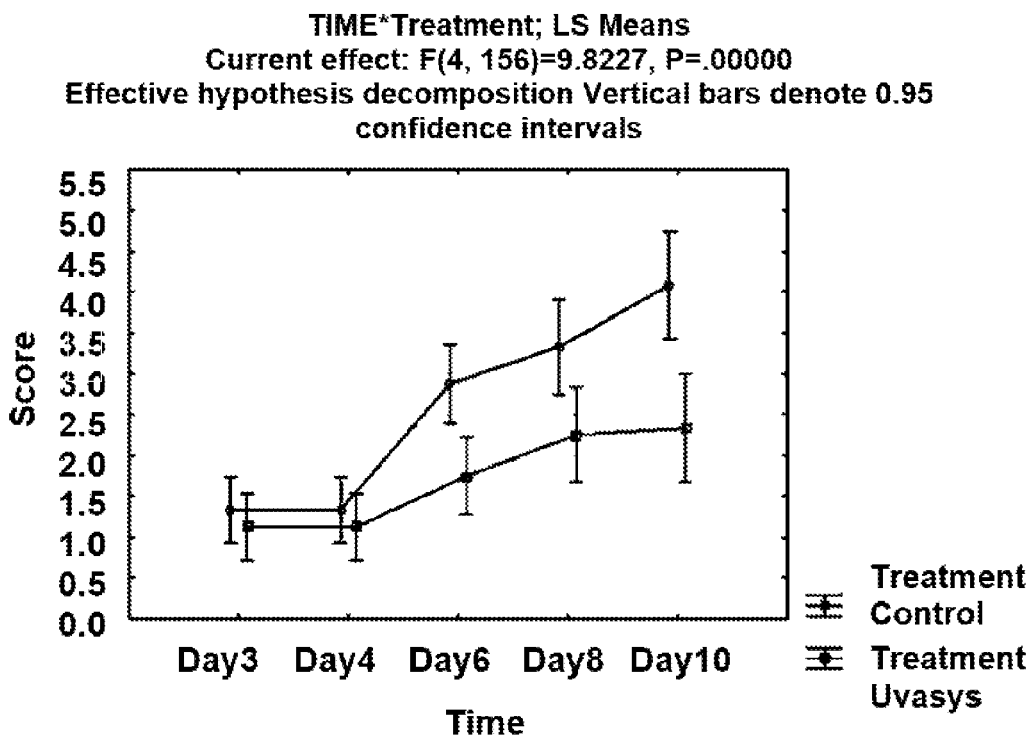
FIG. 2 shows the scores for development of *Botrytis* infection over time on different varieties of treated and control roses.

A significant difference was visible over time between $SO_2$ treated roses compared with control roses (see FIG. 2). The delay in development of *Botrytis* infection was expected, since the *Botrytis* infection would have spread slowly over the course of three days at 4° C. and there was therefore no significant difference between the treatment and control at the end of the simulated in-store period. However, at day 10, the difference was significant and the score of the control roses was almost twice that of the treated roses, taking into account that the higher the score, the greater the effect of *Botrytis* development.

Figure 3:
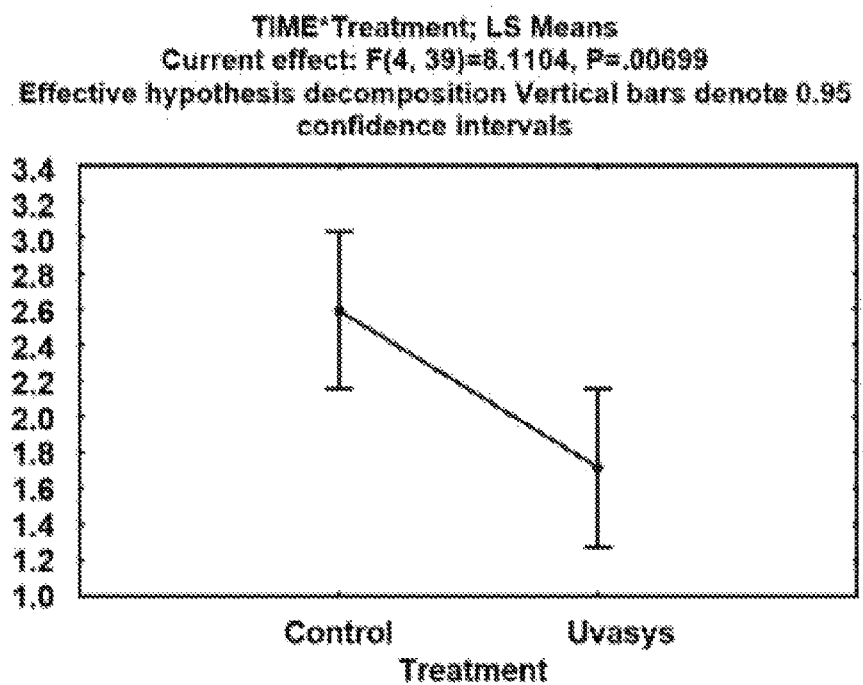
FIG. 3 shows the average *Botrytis* infection scores for treated versus control roses.
Figure 4:
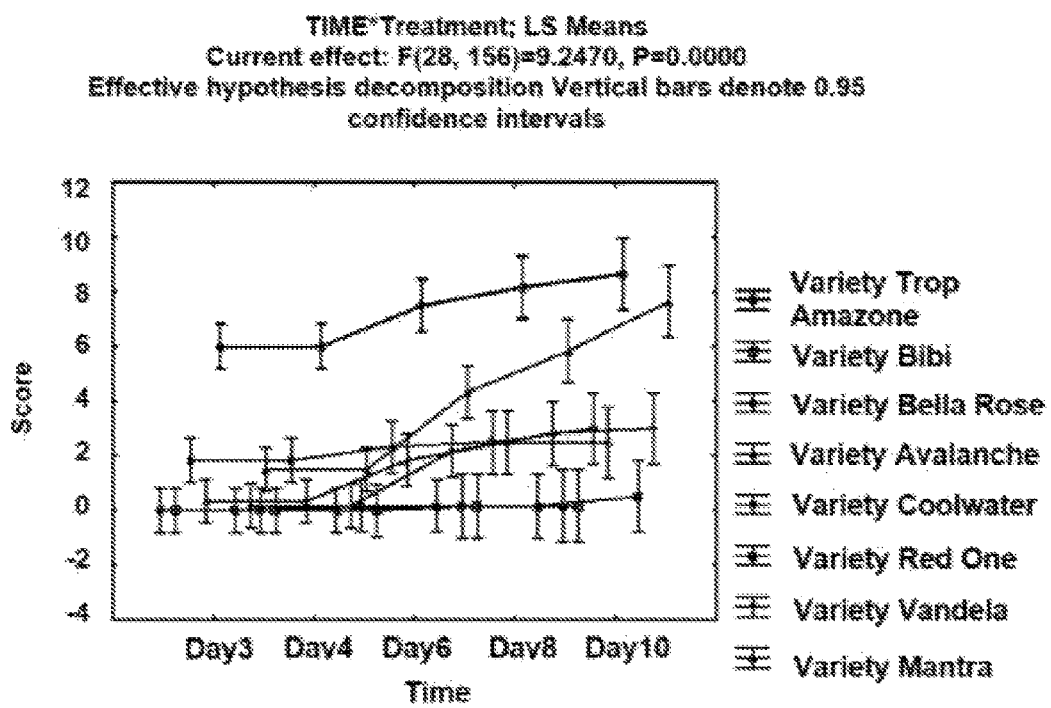
FIG. 4 shows *Botrytis* infection scores for eight different rose cultivars over time.
Figure 5:
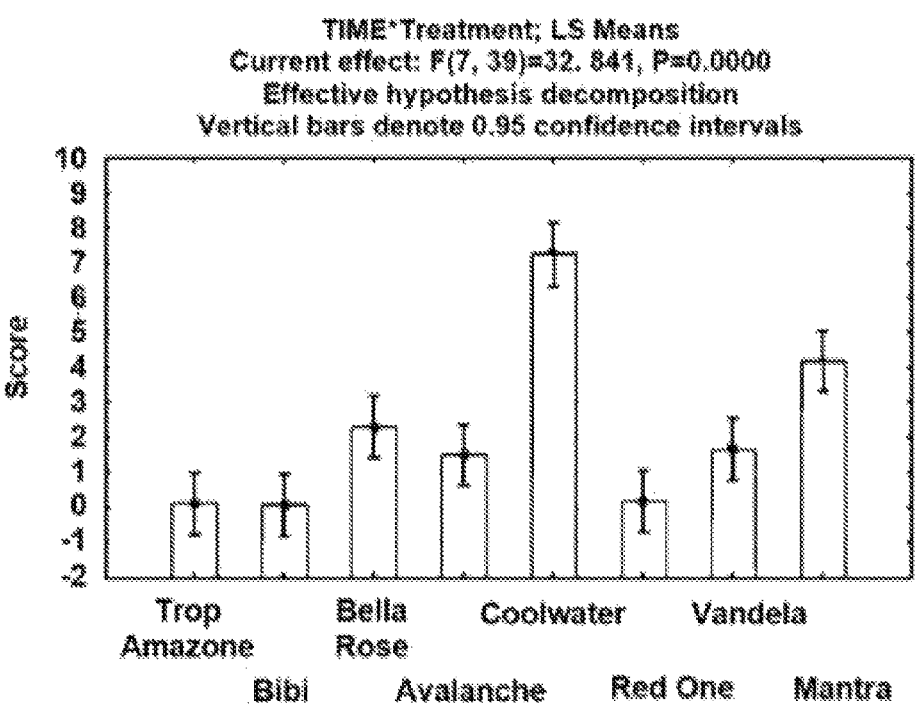
FIG. 5 shows the average *Botrytis* infection scores for eight different rose cultivars over the total period of monitoring.

Treatment of roses with the $SO_2$ generating strip resulted in significantly improved control of *Botrytis* infection compared with control roses when determined over the whole period of testing as shown in FIG. 3. Significant differences in the *Botrytis* infection score were also identified between cultivars over time (FIGS. 4 and 5) with some cultivars being much more sensitive to *Botrytis* than others.

On average Coolwater and Mantra were found to be very sensitive to *Botrytis* infection during the trial whereas Tropical Amazon, Bibi and Red One performed better on average than the other varieties.

In conclusion, the $SO_2$ treatment method was effective in controlling *Botrytis* infection in a number of rose cultivars. This effect was particularly visually noticeable in each treated bunch of roses towards the end of home-display vase life compared with untreated control roses.

The invention claimed is:

1. A method of preserving one or more cut flowers that are exposed to the air during wet transport or storage in buckets, or during display at a point of sale or point of display, comprising providing a sulphur dioxide ($SO_2$) generating device in the form of (i) a $SO_2$ generating strip that is attached to an open top end of a flower sleeve or (ii) in the form of a $SO_2$ generating article of any shape that is positioned above the flower heads wherein the cut flowers that are exposed to the air are at room temperature and 70% relative humidity .

2. The method according to claim 1, comprising the steps of:
   (i) providing one or more cut flowers;
   (ii) providing a flower sleeve having a $SO_2$ generating strip affixed at the open top end and wrapping the flower sleeve around the cut flowers, such that the end to which the $SO_2$ generating strip is affixed is adjacent to, but not in direct contact with, one or more flower heads of the cut flowers contained within the flower sleeve; and/or
   (iii) positioning an $SO_2$ generating article of any shape within the cut flowers and above the one or more flower heads, such that the article is above, but not in direct contact with, one or more flower heads of the cut flowers.

3. The method according to claim 1, wherein the $SO_2$ generating article is positioned above the flowers by affixing the article to an end of an elongate member, whereby the length of the elongate member is positioned within the cut flowers and the affixed article is held above the cut flower heads on the end of the elongate member.

4. The method according to claim 2, wherein the article is affixed to the open top end of the flower sleeve mechanically, or with an adhesive.

5. The method according to claim 4, wherein the article is affixed with glue, a clasp mechanism, or staples.

6. The method according to claim 1, wherein the preservation comprises inhibition of growth of a microbial organism.

7. The method according to claim 6, wherein the microbial organism is a fungal organism.

8. The method according to claim 7, wherein the fungal organism is *Botrytis* sp.

9. The method according to claim 1, wherein the cut flowers are any cut flower that is susceptible to *Botrytis* infection.

10. The method according to claim 1, wherein the cut flowers are selected from the group consisting of roses, chrysanthemums, and gerberas.

\* \* \* \* \*